United States Patent
Schennib

(10) Patent No.: US 8,246,585 B2
(45) Date of Patent: Aug. 21, 2012

(54) HEMOSTATIC CLIP

(75) Inventor: Hani Schennib, Phoenix, AZ (US)

(73) Assignee: Vascular Solutions, Inc., Minneapolis, MN (US)

( * ) Notice: Subject to any disclaimer, the term of this patent is extended or adjusted under 35 U.S.C. 154(b) by 81 days.

(21) Appl. No.: 12/483,698

(22) Filed: Jun. 12, 2009

(65) Prior Publication Data

US 2009/0318881 A1 Dec. 24, 2009

Related U.S. Application Data

(60) Provisional application No. 61/073,622, filed on Jun. 18, 2008.

(51) Int. Cl.
*A61M 5/14* (2006.01)

(52) U.S. Cl. .................. 604/256; 604/167.03; 604/177; 604/178

(58) Field of Classification Search .................. 604/250, 604/523, 167.01, 177, 178; 24/455
See application file for complete search history.

(56) References Cited

U.S. PATENT DOCUMENTS

| 3,537,451 | A | * | 11/1970 | Beck et al. | 604/165.03 |
| 5,141,497 | A | * | 8/1992 | Erskine | 604/164.05 |
| 5,167,644 | A | | 12/1992 | Fischell et al. | |
| 5,336,192 | A | | 8/1994 | Palestrant | |
| 5,413,561 | A | * | 5/1995 | Fischell et al. | 604/167.01 |
| 2007/0060927 | A1 | * | 3/2007 | Longson et al. | 606/108 |

FOREIGN PATENT DOCUMENTS

WO    WO 94/01169    1/1994

* cited by examiner

*Primary Examiner* — Kevin C Sirmons
*Assistant Examiner* — Brandy C Scott
(74) *Attorney, Agent, or Firm* — Patterson Thuente Christensen Pedersen, PA

(57) ABSTRACT

A device for inhibiting blood leakage from the proximal end of a catheter. The device includes a resilient body having a proximal portion and a distal extension portion extending away from the proximal portion and terminating at a first end. The proximal portion and the distal extension portion share a common axis and together define a generally cylindrical passage at least partially therethrough. The distal extension portion is shaped to interface with the catheter and in a substantially sealing relationship. The cylindrical passage is sized to receive a surgical guidewire therein in close apposition.

10 Claims, 12 Drawing Sheets

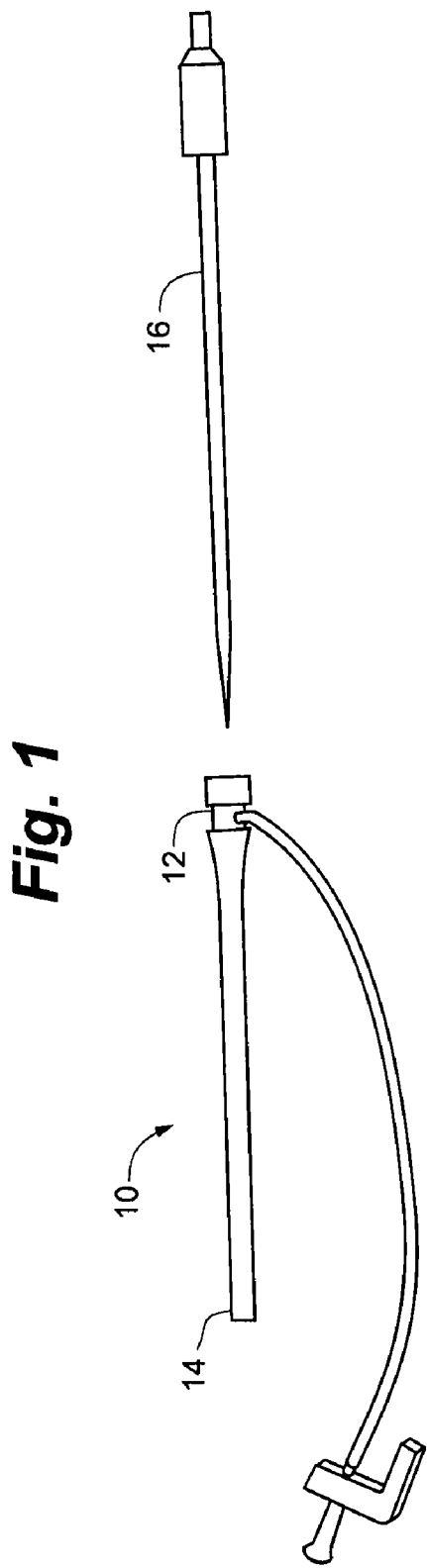

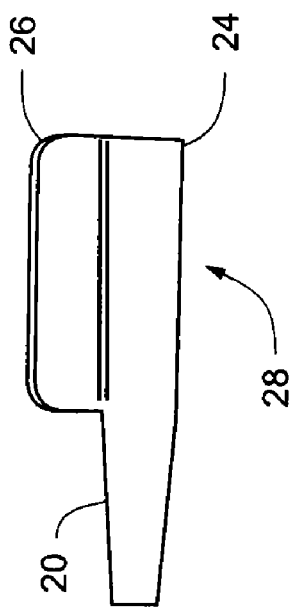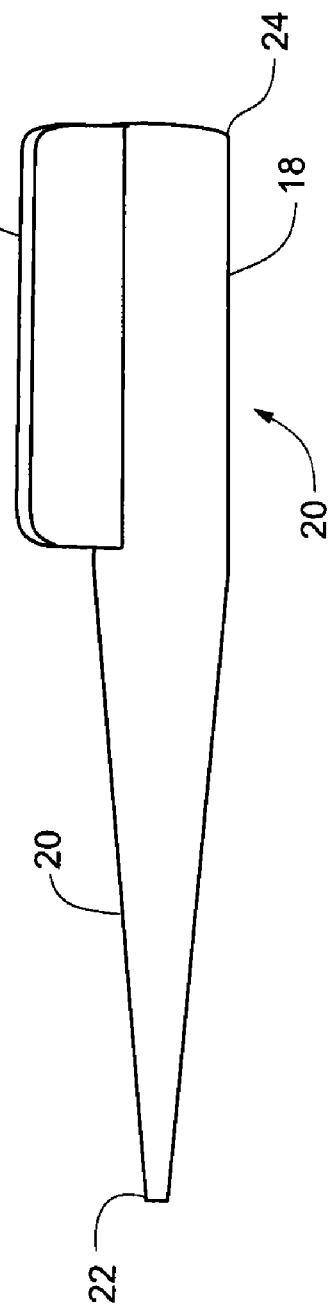

HEMOSTATIC CLIP

CLAIM TO PRIORITY

This application claims the benefit of U.S. Provisional Patent Application 61/073,622, filed Jun. 18, 2008 entitled "Hemostatic Clip" the entire contents of which are incorporated by reference herein.

FIELD OF THE INVENTION

The invention relates generally to producing temporary at least partial hemostasis in an intravascular catheter or introducer sheath.

BACKGROUND OF THE INVENTION

Intravenous and intra-arterial catheter-cannula devices are used to deliver drugs, fluids or medical devices into the circulatory system of patients. A catheter, cannula or sheath is inserted into a patient's vein or artery, typically using an introducer needle. After the device is inserted, the needle is withdrawn and some other instrument or device is inserted through the catheter or cannula.

Catheters include a broad variety of tubular devices that are inserted into blood vessels to provide access to the vascular system of a living being as well as therapeutic devices that are used to treat ailments of the body via the vascular system. Catheters include but are not limited to any tubular device that is inserted into a living body through which fluid may exit the body when the device is inserted into the body such as introducers and sheaths having hemostatic valves.

The vascular system is under constant but varying pressure in a living being. The arterial system is under higher pressure than the venous system. While placing the other device into the catheter or cannula, blood or other bodily fluid can back flow out of the end of the catheter or cannula. This is particularly true when an artery is accessed due to the higher arterial blood pressure as compared to venous blood pressure. Often, a guidewire is inserted through the catheter or cannula assembly that has been prelocated in the femoral artery in a patient's groin to allow the insertion of instruments complex procedures to be performed in the heart or the arteries surrounding the heart. When a guidewire is present in a sheath often a hemostatic valve cannot be closed to prevent leakage of blood from the accessed blood vessel.

Intravascular instruments need to be switched out during these procedures, often allowing blood to flow out of the opening at the proximal end of the catheter. Prior art methods of closing the catheter end, such as ball valve assemblies and one-way valves cannot be operated with a guide wire still in place.

SUMMARY OF THE INVENTION

The invention solves many of the above discussed problems. The invention is directed to a hemostatic clip that may be used to prevent blood leakage from the end of a catheter, introducer, sheath or cannula device.

The hemostatic clip of the present invention generally includes a unitary one piece structure generally formed from an inert flexible material such as rubber or a flexible polymer. In one example embodiment, the hemostatic clip of the invention may be formed of urethane or Pebax 5533. In another example embodiment, the hemostatic clip is formed of a thermoplastic vulcanizate such as Santoprene™ polymer having a Shore hardness of between about 40-80 on the Shore A scale. These examples should not be considered limiting as many other flexible polymers may also be used.

In one embodiment, the hemostatic clip has an at least partially conical body and two actuator tabs. The generally conical body has narrow apex and a broad base. The generally conical body also defines a cylindrical passage through at least part of the length thereof. The cylindrical passage is in communication with a slot that connects the cylindrical passage to one longitudinal surface of the hemostatic clip. The hemostatic clip has a generally conical or frustoconical distal end. In one embodiment of the invention, the conical distal end is sized to fit into and at least partially plug the distal end of a catheter or cannula. In another embodiment of the invention, the conical distal end is somewhat blunted so as to plug a catheter or cannula by blunt apposition with the open end of the catheter or cannula. A truncated conical shape may also facilitate the insertion of the hemostatic clip into a large diameter sheath such as a twenty or twenty five French sheath.

The hemostatic clip of the invention generally includes a conical or frustoconical tip portion, a proximal portion which may be conical or cylindrical or another shape and two generally opposed actuators extending outwardly away from the proximal portion at an obtuse or acute angle relative to one another.

The conical tip portion and proximal portion define a generally cylindrical passage therethrough which communicates with a longitudinal side of the hemostatic clip via a slit. In one embodiment, when the hemostatic clip is in a relaxed state, the slit is open into the cylindrical passage in the hemostatic clip. The actuators may be oriented such that a physician or other health professional can grip the actuators and flex the hemostatic clip to open or close the slot to facilitate placing the cylindrical passage around an object placed in the cylindrical passage such as a vascular guidewire.

In one embodiment, the conical tip portion of the hemostatic clip is dimensioned to pass, at least partially, into the distal end of a sheath, cannula or a catheter, for example, a sheath, cannula or catheter that has been used to introduce a guidewire into a blood vessel in a living being.

In one embodiment, the hemostatic clip defines an interior slot therein. The interior slot may further define one or more extensions and mating recesses. The extensions may include a plateau on which a surgical guidewire may rest when it is passed through the cylindrical passage within the hemostatic clip. Alternatively, the surgical guidewire may be moved into the interior slot and be gripped between the recess and the extension in order to facilitate grasping the surgical guidewire with the hemostatic clip. The guidewire may also be gripped by squeezing the hemostatic clip while the guidewire is in the cylindrical passage.

In one embodiment of the invention, the hemostatic clip may include a ventral fin extending outwardly away from the cylindrical portion of the body. Multiple extensions and recesses may be provided within the interior slot.

Another example embodiment of the invention includes one or more circumferential ridges on the surface of the surface of the conical or frustoconical tip portion of the hemostatic clip. The circumferential ridges may be spaced along the tip portion to assist in sealing with particular internal diameters of various size catheter lumens. In an example embodiment, the circumferential ridges are about 0.015 inches in height. Three ridges may be utilized spaced apart along the length of the conical or frustoconical tip portion. More or fewer ridges may be used as well.

BRIEF DESCRIPTION OF THE DRAWINGS

FIG. 1 is a plan view of an example catheter cannula device or introducer sheath in accordance with the prior art;

FIG. 2A is an elevational view of an example embodiment of the present invention;

FIG. 2B is a elevational view of an another example embodiment of the present invention;

FIG. 3 is a bottom plan view of the embodiment of FIG. 2a;

DETAILED DESCRIPTION OF THE DRAWINGS

Figure 3:
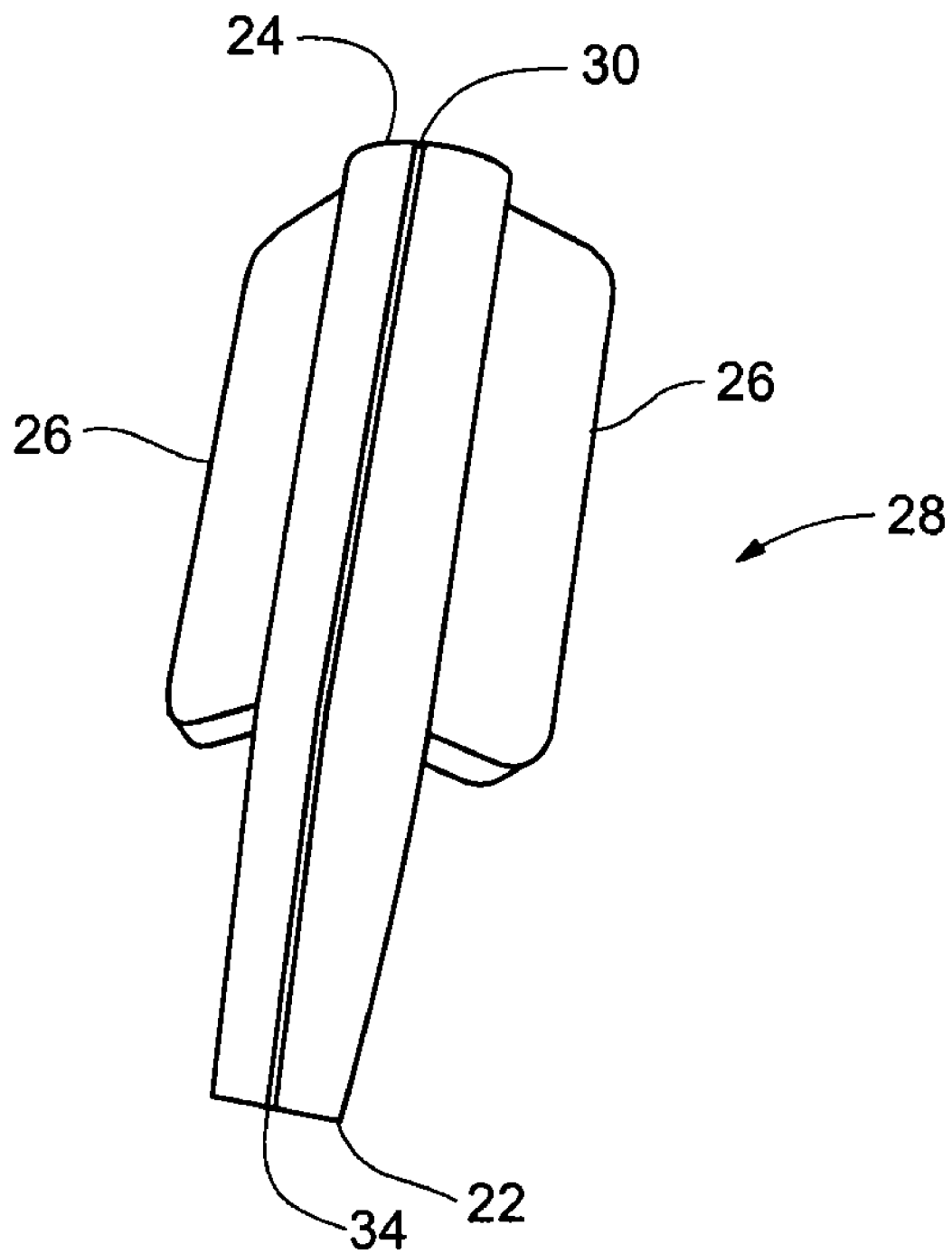

FIG. 1 depicts a typical catheter-cannula device 10, useful with the present invention. Proximal end 12 defines an opening where a guide wire may be inserted, and distal end 14 is the exit of cannula 10 located inside of a vein or artery. Obturator 16 may be used to plug proximal end 12 of the catheter-cannula 10 when a guide wire is not present. Catheter-cannula device 10 is also often referred to as an introducer sheath, introducer or sheath.

As illustrated in FIGS. 2A, B, some embodiments of a hemostatic clip 18 of the present invention include a conical body 20 with a first end 22 and a second end 24 along with two actuator tabs 26 on the surface of conical body 20. Actuator tabs 26 allow the device to be opened to accept a surgical guide wire. One embodiment of hemostatic clip 18 includes blunt first end 22 on conical body 20. Another embodiment of hemostatic clip 18 includes pointed first end 22 on conical body 20.

Figure 4:
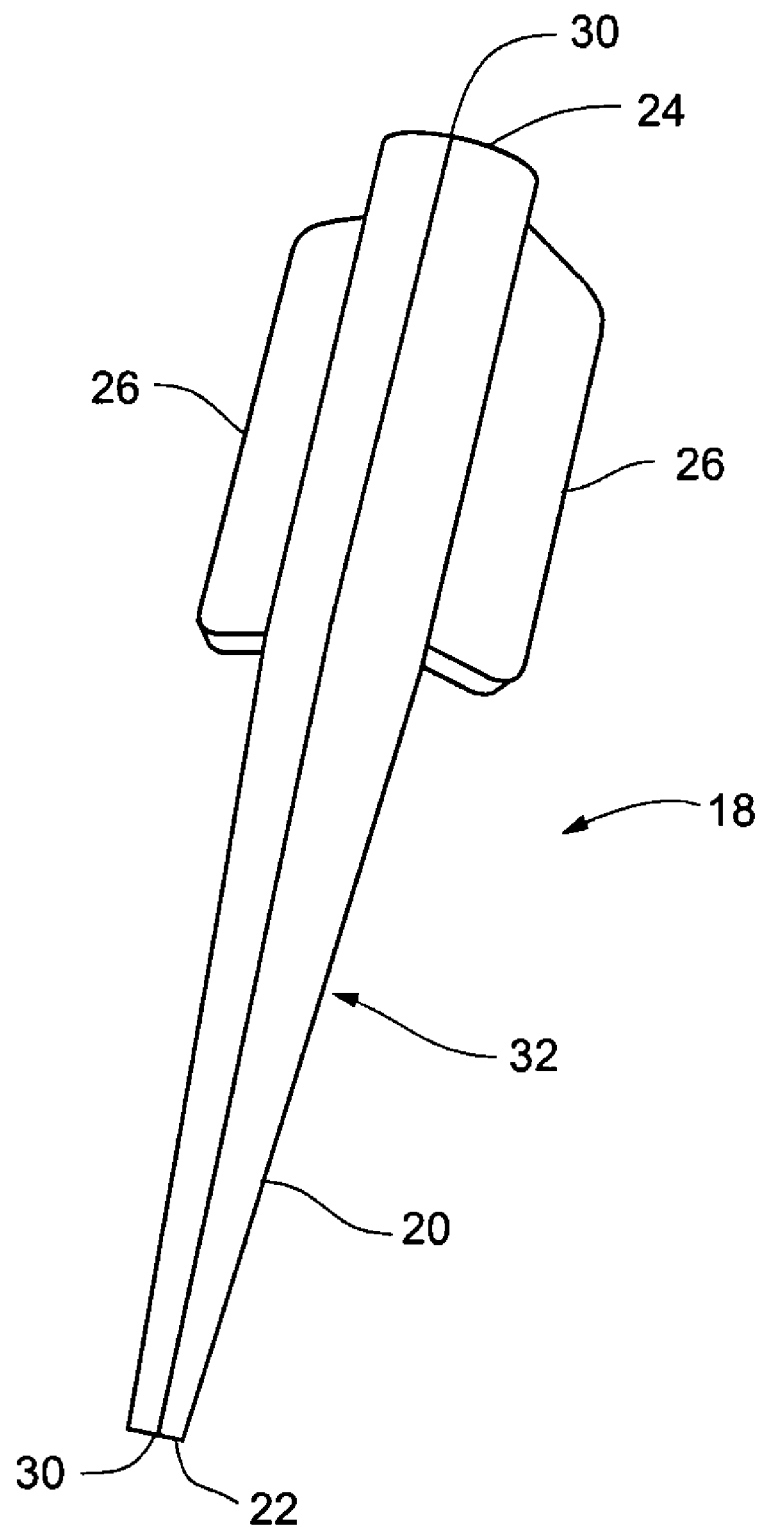
FIG. 4 is a bottom plan view of the embodiment depicted in FIG. 2b.

As illustrated in FIG. 3, one embodiment of the blunt hemostatic clip 28 defines slit 30 running from first end 22 to second end 24. FIG. 4 illustrates one embodiment of pointed hemostatic clip 32 with slit 34 running from first end 22 to second end 24. In several embodiments, slit 30 is substantially parallel to the longitudinal axis of conical body 20.

Figure 5:
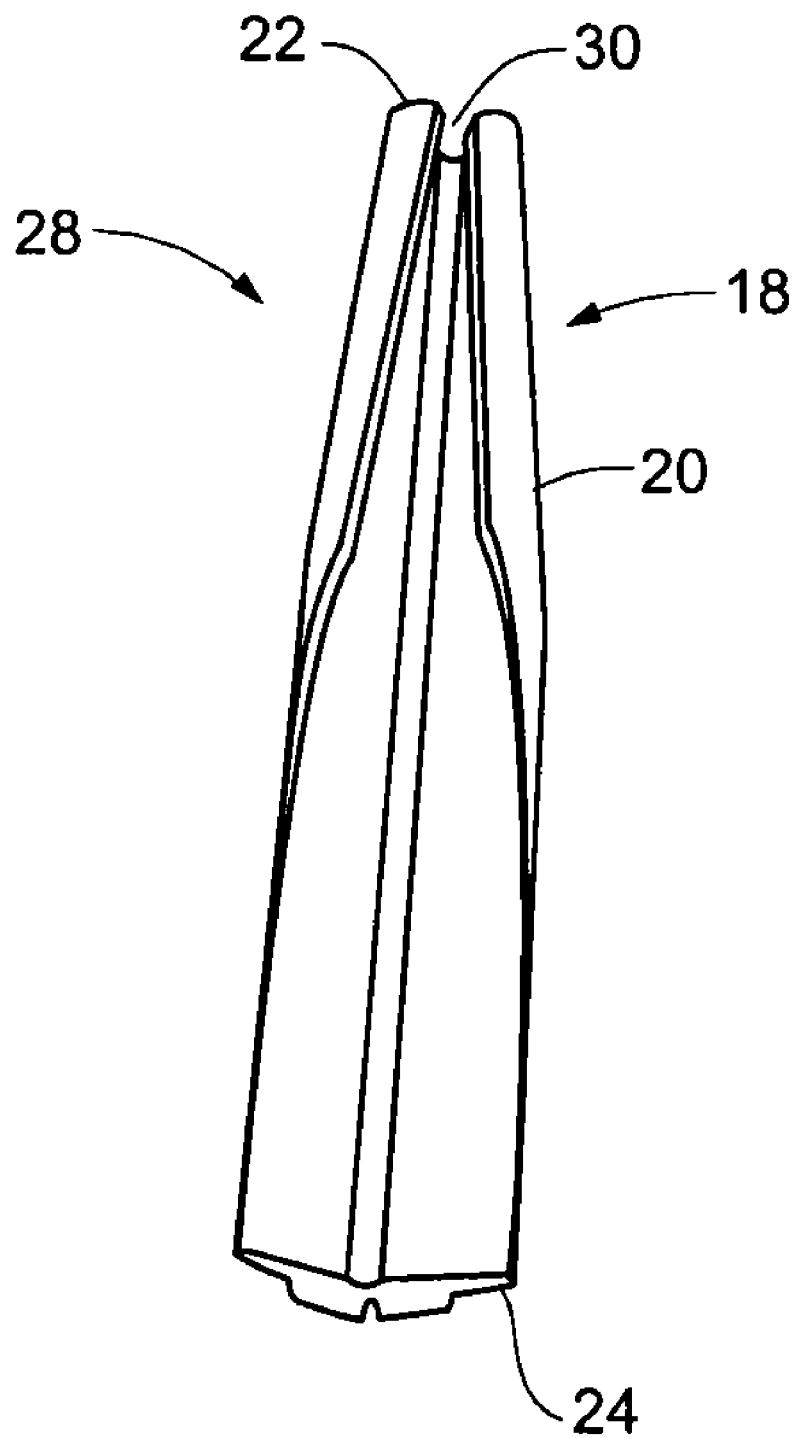
FIG. 5 is a bottom plan view of an embodiment of the invention flexed to open an external slot.
Figure 6:
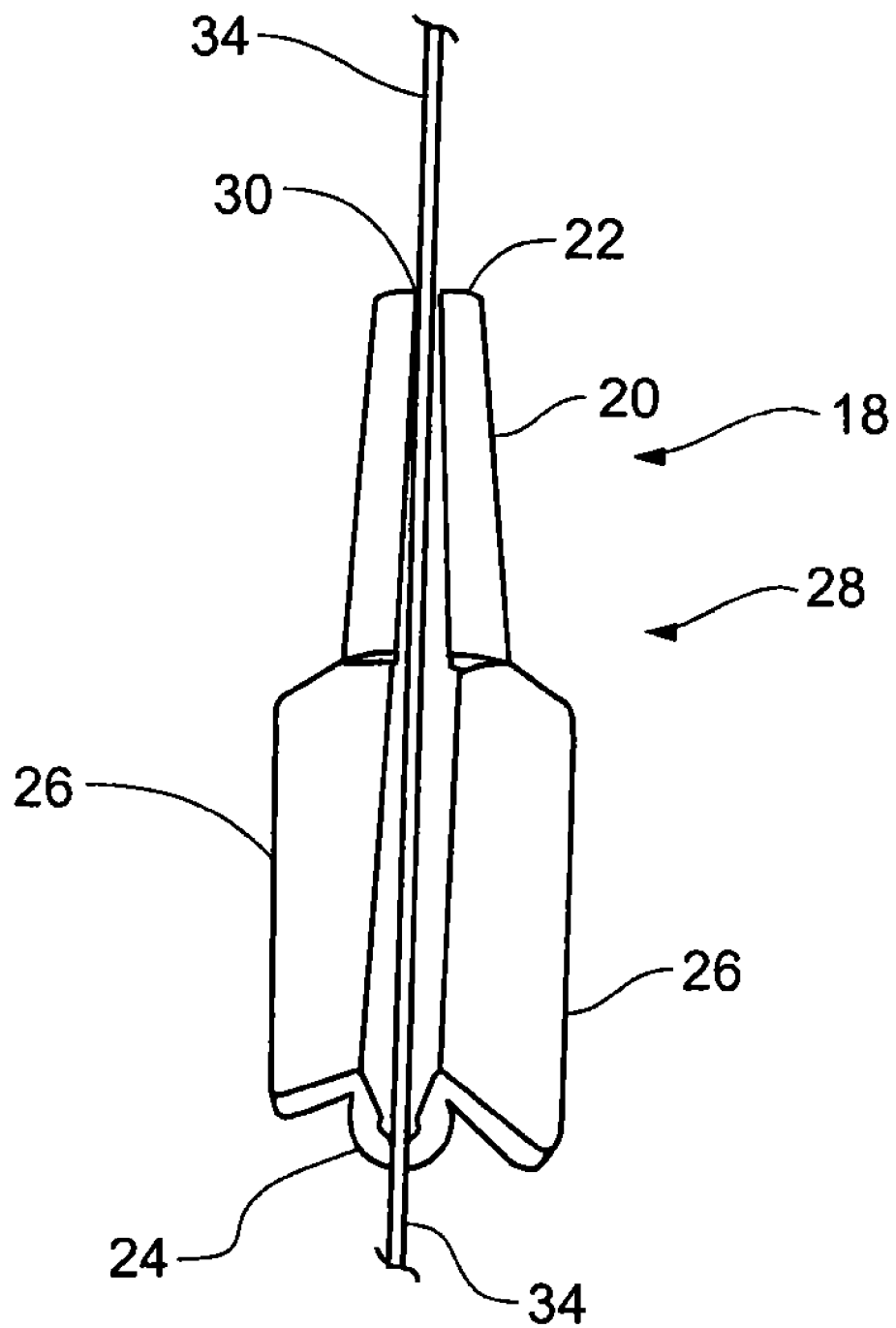
FIG. 6 is bottom plan view of an embodiment of the present invention depicted surrounding a surgical guidewire.
Figure 7:
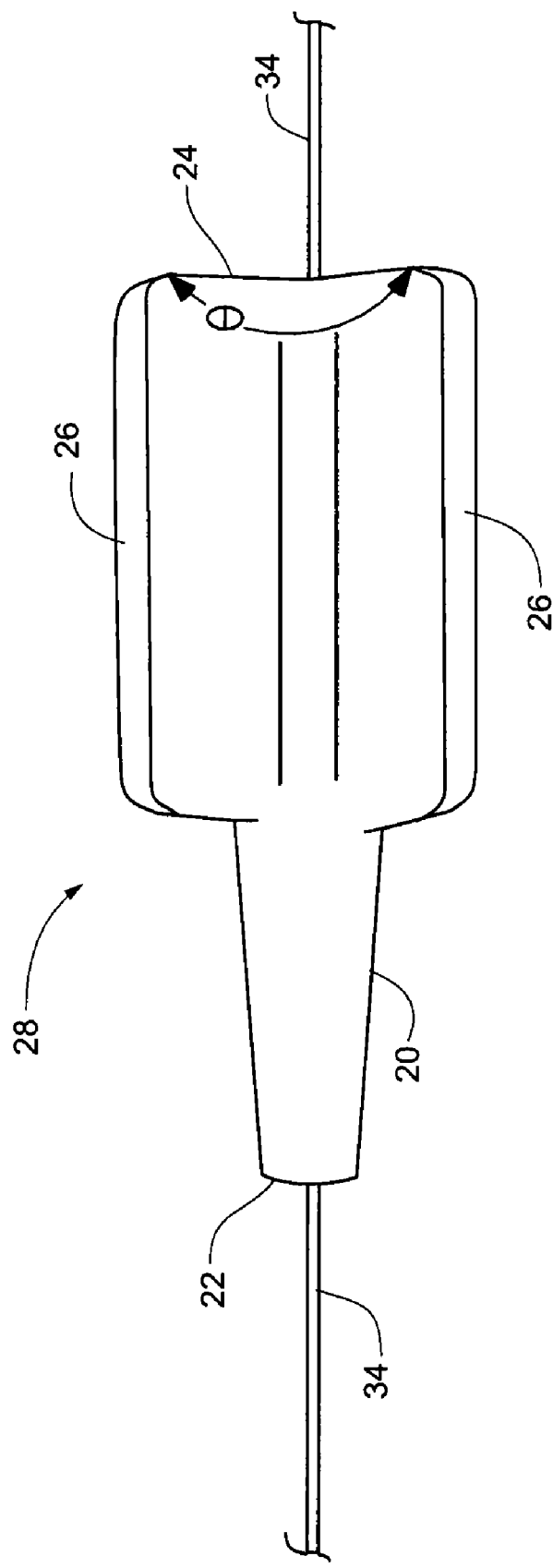
FIG. 7 is a top plan view of an embodiment in accordance with the present invention.

As illustrated in FIGS. 5 and 6, upon actuating tabs 26 of the blunt hemostatic clip 28, slit 30 opens up and may receive a surgical guide wire 34. As shown in FIG. 7, upon releasing actuating tabs 26 of blunt hemostatic clip 28, surgical guidewire 34 remains captive in slit 30. With or without surgical guidewire 34 in slit 30, first end 22 may be inserted into or abutting the end of a catheter-cannula 10, thereby sealing proximal end 12 and inhibiting blood from flowing out. In accordance with the invention, there need not be complete sealing, only reduction or inhibition of blood leakage from catheter-cannula 10.

Figure 8:
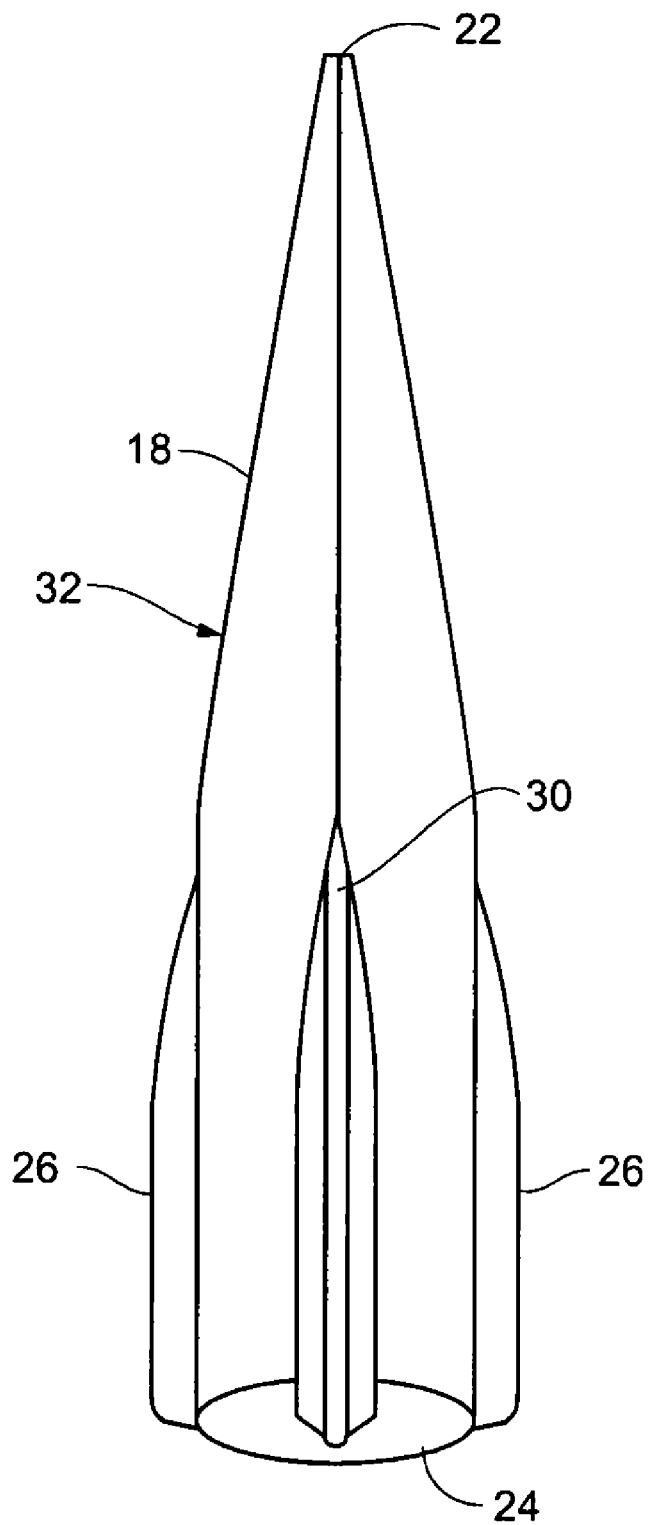
FIG. 8 is a bottom plan view of an embodiment of the present invention, in a partially flexed open orientation.
Figure 9:
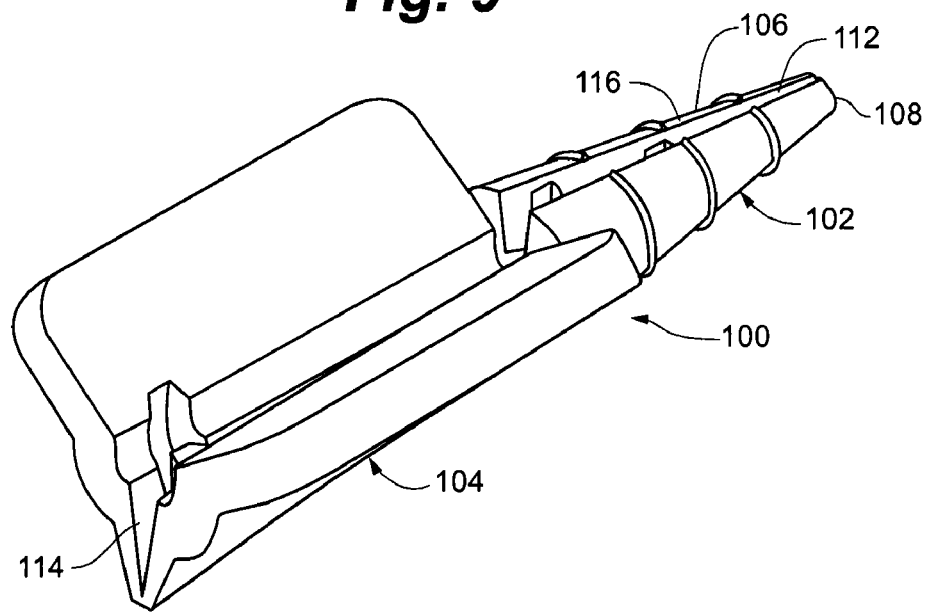
FIG. 9 is a perspective view of another embodiment of a hemostatic clip in accordance with the invention.

FIG. 8 depicts another example embodiment of the invention, pointed hemostatic clip 30. Slit 30 is depicted with pointed hemostatic clip 32 in a partially actuated position. Upon being in a fully actuated position, slit 30 may accept surgical guide wire 34 as described in the blunt hemostatic clip 28. With or without surgical guide wire 34 in slit 30, first end 22 may be inserted into proximal end 12 of a catheter-cannula 10, thereby closing proximal end 22 and inhibiting blood from flowing out. In one embodiment, first end 22 is sized so that about 0.25 inches of first end 22 enters and substantially seals or closes proximal end 12.

In one example embodiment, actuator tabs 26 as shown in FIG. 7 may be located near second end 24 of hemostatic clip 18. In some embodiments, actuator tabs 26 may be oriented so that the angle θ formed between the two actuator tabs 26, on the side of the conical body 20 opposite slit 30, is approximately 90°. A minimum working angle is that which allow the slit 30 to open enough to accept surgical guidewire 34. A maximum working angle occurs when two actuator tabs 26 are located next to each corresponding side of slit 30. However, as angle θ increases, it may become more difficult for a physician to open hemostatic clip 18 with one hand. In some embodiments, actuator tabs 26 are large enough to allow a surgeon wearing gloves to easily actuate them, thereby opening slit 30 of the hemostatic clip 18.

Useful materials for forming hemostatic clip 18 are pliable plastic or rubber materials that return to a resting, first position after being flexed into a second position. In some embodiments, shape memory polymers are used. In certain embodiments, the hemostatic clip is disposable, and only needs to withstand a limited number of flexing repetitions. For most procedures hemostatic clip 10 is provide sterilized and in a sealed package intended for a single use and then discarded.

In another example embodiment, depicted in FIGS. 9-13 hemostatic clip 100 generally includes conical tip portion 102 and proximal portion 104.

Referring to FIGS. 9-12, conical tip portion 102 includes conical or frustoconical member 106, which may have blunt end 108 or a pointed end (not shown in FIGS. 9-12).

Figure 10:
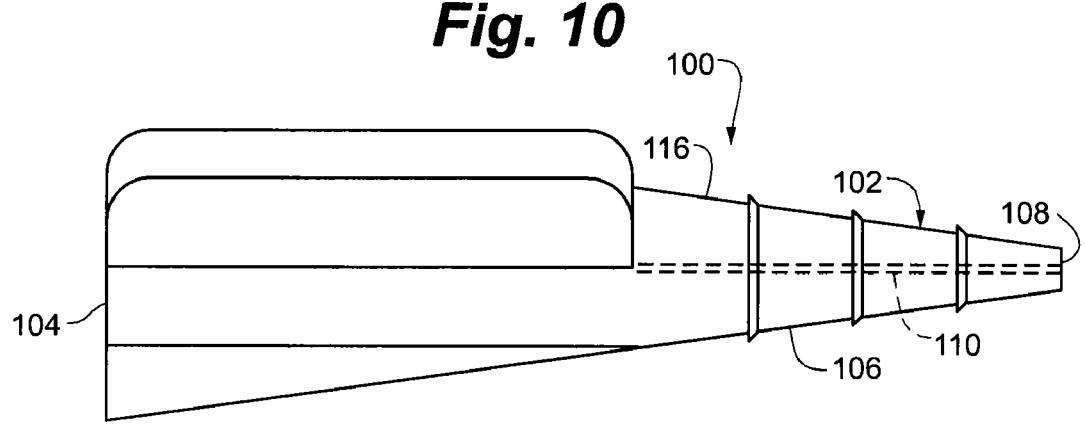
FIG. 10 is an elevational view of the embodiment of FIG. 9 with some structures depicted in phantom.
Figure 11:
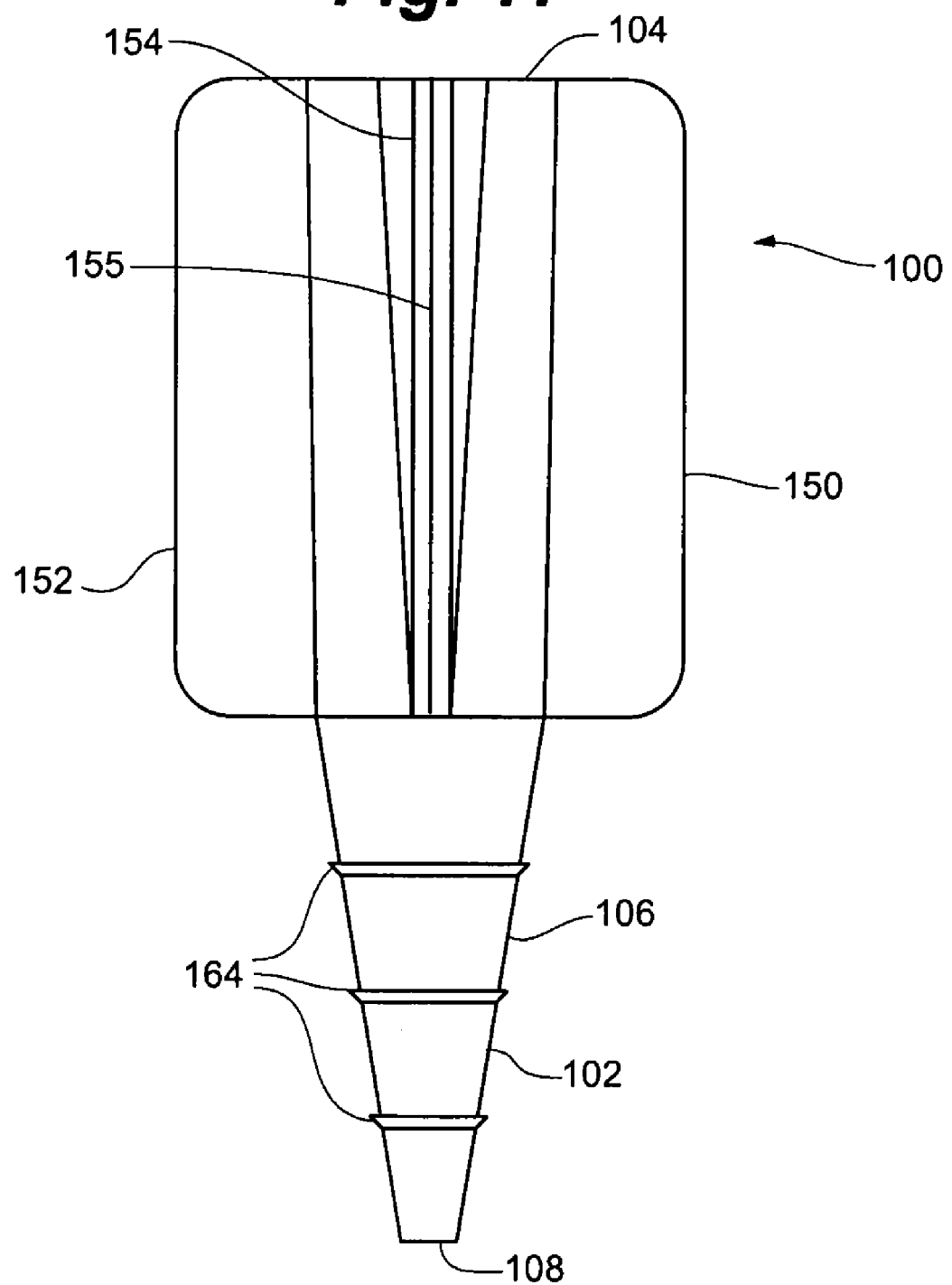
FIG. 11 is a bottom plan view of a hemostatic clip as depicted in FIG. 9.
Figure 12:
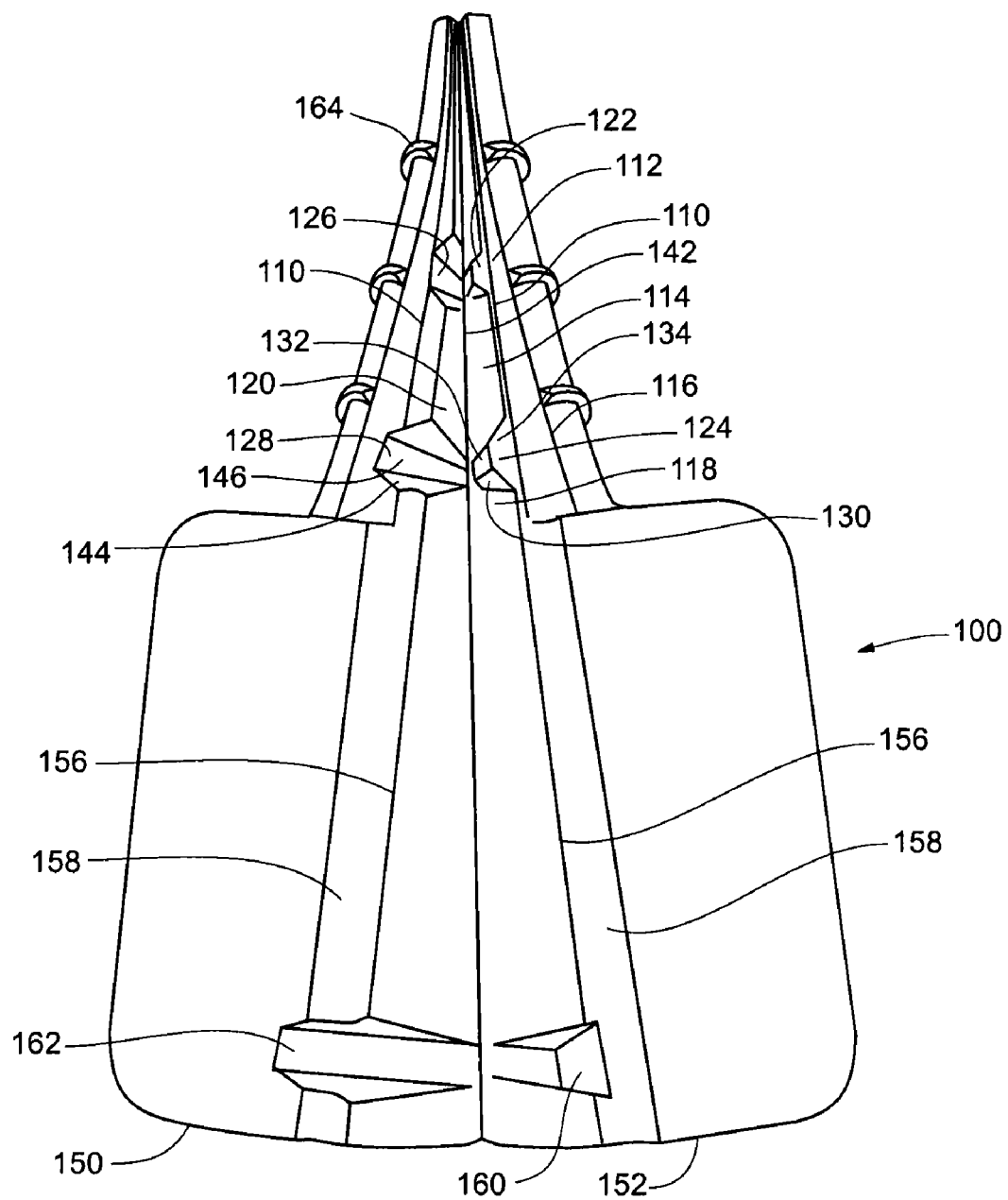
FIG. 12 is a top plan view of a hemostatic clip in accordance with the present invention as depicted in FIG. 9.
Figure 13:
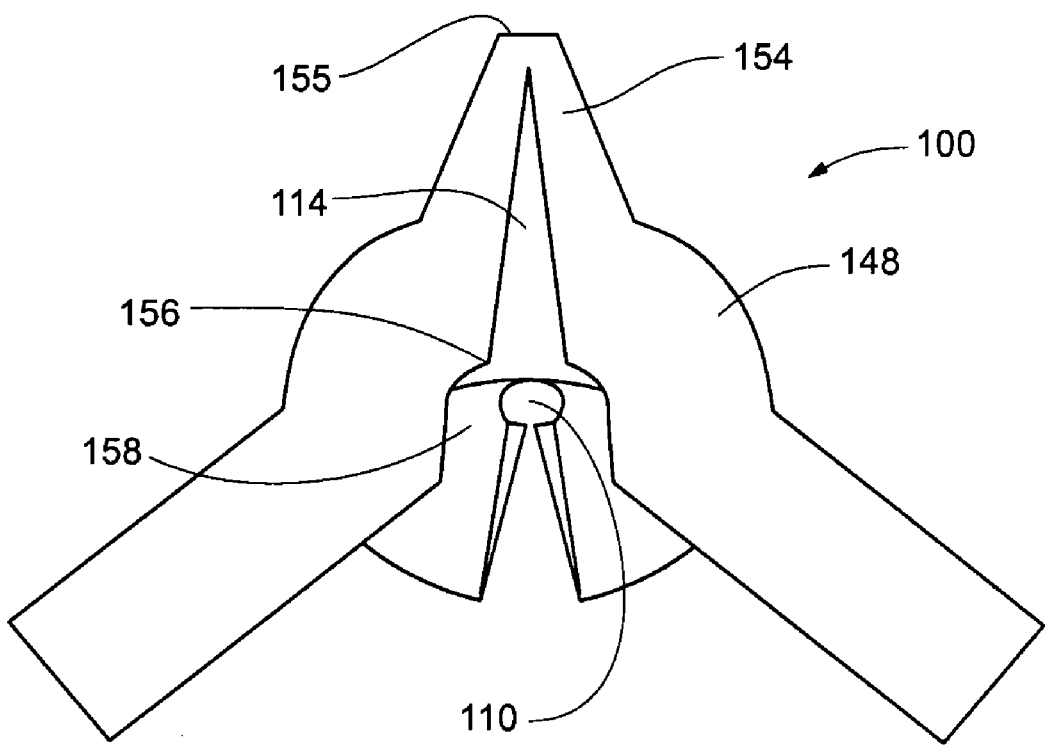
FIG. 13 is an end elevational view of a hemostatic clip in accordance with the present invention.

Referring particularly to FIGS. 10, 12 and 13, conical tip portion 102 defines therein cylindrical passage 110, exterior slot 112 and interior slot 114.

In the depicted example embodiment, cylindrical passage 110 extends generally from blunt end 108 through conical tip portion 102 to proximal portion 104. Cylindrical passage 110 is dimensioned to receive surgical guidewire 34 in close approximation to cylindrical passage 110. Cylindrical passage 110 can extend entirely through hemostatic clip 100 as well. Cylindrical passage 110 may be formed as two hemi-cylindrical portions as well.

As can be seen in FIG. 12, in this example, exterior slot 112 extends from cylindrical passage 110 outwardly to exterior surface 116 of conical tip portion 102. Interior slot 114 extends inwardly into conical tip portion 102 but not entirely through conical tip portion 102.

In an example embodiment, interior slot 114 is defined by first wall 118 and second wall 120. First wall 118 defines first extension 122 and second extension 124 protruding outwardly therefrom. Second wall 120 defines first recess 126 which is shaped to generally mate with first extension 122 and second recess 128 which is shaped to generally mate with second extension 124. Mating in this context refers to first recess 126 receiving first extension 122 therein and second recess 128 receiving second extension 124 therein.

Referring particularly to FIG. 12, in an example embodiment, first extension 122 and second extension 124 each include triangular walls 130, outer wall 132 and plateau 134. First extension 122 and second extension 124 generally taper from plateau 134 to termination 142 of interior slot 114.

First recess 126 and second recess 128 are positioned to generally align and mate with first extension 122 and second extension 124 respectively. In an example embodiment, first recess 126 and second recess 128 may extend outwardly along second wall 120 from both sides of cylindrical passage 110. First recess 126 and second recess 128 generally define triangular walls 144 and inner wall 146.

Proximal portion 104 of hemostatic clip 100 generally includes cylindrical portion 148, first actuator 150, second actuator 152 and ventral fin 154.

In an example embodiment, cylindrical portion 148 is integral with and extends from the base end of conical tip portion 102. Cylindrical portion 148 may have a diameter essentially equal to the base of conical tip portion 102. As can be seen in FIGS. 9-13, first actuator 150 and second actuator 152 extend outwardly away from cylindrical portion 148 in a generally radial direction. In this example embodiment, first actuator 150 and second actuator 152 form an angle of approximately 90° with each other. First actuator 150 and second actuator 152 are dimensioned to be readily gripped by the fingers of a physician utilizing hemostatic clip 100.

Ventral fin 154 extends outwardly from cylindrical portion 148 in a direction generally 180° opposed to the direction of exterior slot 112 in this example embodiment. Ventral fin 154 may display a sloped ridge 155 sloped at an angle generally equal to and continuous with exterior surface 116 of conical tip portion 102.

In an example embodiment, interior slot 114 continues from conical tip portion 102 into and through cylindrical portion 148 and within ventral fin 154. Cylindrical portion 148 further defines interior ridges 156 which border and partially define exterior valley 158. In an example embodiment, exterior valley 158 extends generally coaxially with cylindrical passage 110 and may be U-shaped to receive surgical guidewire 34.

First wall 118 and second wall 120 of interior slot 114 continue through cylindrical portion 148 of hemostatic clip 100. First wall 118 defines third extension 160 and second wall 120 defines third recess 162 within cylindrical portion 148. Third extension 160, in this example embodiment, may be similar to first extension 122 and second extension 124 in including triangular wall 130, outer wall 132 and plateau 134.

Third recess 162 in this example defines triangular walls 144 and inner wall 146. In this example embodiment, third extension 160 and third recess 162 extend downwardly into interior slot 114 within ventral fin 154.

Referring to FIGS. 9-12, another example embodiment of the invention includes one or more circumferential ridges 164 on the surface of the surface of conical tip portion 102 of hemostatic clip 100. Circumferential ridges 164 may be spaced along conical tip portion 102 to assist in sealing with particular internal diameters of various size catheter-cannula 10 lumens. In an example embodiment, circumferential ridges 164 have a height of about 0.015 inches.

Hemostatic clip 18, 100 of the invention generally is formed as a unitary one piece structure from a biocompatible or inert flexible material such as rubber or a flexible polymer. In one example embodiment, hemostatic clip 18, 100 of the invention may be formed of Pebax 5533 or urethane. In another example embodiment, hemostatic clip 18, 100 is formed of a thermoplastic vulcanizate such as Santoprene™ polymer having a Shore hardness of between about 40-80 on the Shore A scale. These examples should not be considered limiting as other flexible polymers may also be used. Santoprene™ polymer having a Shore hardness of between about 40-80 on the Shore A scale has been found to have a resiliency that is appropriate to effectively inhibit leakage around a guidewire 34 and within a catheter-cannula 10.

In operation, hemostatic clip 100 is flexed to place surgical guidewire 34 within cylindrical passage 110. In doing so, surgical guidewire 34 may pass generally through exterior valley 158 if present. Conical tip portion 102 of hemostatic clip 100 may then be slid along surgical guidewire 34 to come to rest within the opening at the end of catheter-cannula device 10. In doing so, conical tip portion 102 along with surgical guidewire 34 substantially blocks catheter cannula device 10 thus inhibiting seepage of blood or other bodily fluids from catheter cannula device 10.

If desired, hemostatic clip 100 may be manipulated to place surgical guidewire 34 into interior slot 114 when inhibiting leakage of fluid from catheter cannula device 10 is not desired. When surgical guidewire 34 is within interior slot 114 first actuator 150 and second actuator 152 may be squeezed together to grip surgical guidewire 34 between first extension 122 and first recess 126, second extension 124 and second recess 128 as well as third extension 160 and third recess 162 providing a convenient way for a physician to grasp and manipulate surgical guidewire 34. The shape and structure of first extension 122 and first recess 126, second extension 124 and second recess 128 as well as third extension 160 and third recess 162 may facilitate gripping of guidewire 34.

Hemostatic clip 100 may also be squeezed when surgical guidewire 34 is within cylindrical passage 110 and exterior valley 158 to grip surgical guidewire 34 to advance, withdraw or otherwise manipulate surgical guidewire 34.

Surgical guidewire 34 may also be positioned in cylindrical passage 110 and exterior valley 158 such that surgical guidewire 34 rests on plateau 134 of first extension 122, second extension 124 and third extension 160.

When utilizing blunt hemostatic clip 28 or pointed hemostatic clip 32, surgical guidewire 34 is placed within blunt hemostatic clip 28 or pointed hemostatic clip 32 in a similar fashion.

Circumferential ridges 164, if present, assist in inhibiting fluid leakage. Circumferential ridges 164 can be placed on conical tip portion 102 at intervals appropriate to fit within a lumen of catheter cannula 10 to fit just within the lumen to provide additional leakage inhibiting effect.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A device for inhibiting blood leakage from a proximal end of a catheter or sheath, having a lumen, that has been inserted into a blood vessel in a living being when a guidewire is inserted into the lumen and the guidewire and the catheter extend outside of the blood vessel; the device comprising:
   a flexible, resilient body defining a generally cylindrical passage at least partially therethrough and along at least part of a common axis extending from a first end to a second end of the flexible, resilient body, the cylindrical passage extending at least partially from the first end toward the second end and being sized to receive the guidewire in close apposition therein;
   the flexible resilient body having a proximal portion and a distal extension portion extending outwardly away from the proximal portion and terminating at the first end, the proximal portion terminating at the second end opposed to the first end;

the proximal portion and the distal extension portion further together defining an exterior slot extending from the first end to the second end and communicating along a substantially radial path extending outwardly from the generally cylindrical passage between the generally cylindrical passage and an outer surface of the flexible resilient body continuously from the first end to the second end;

the first end being shaped to interface with the proximal end of the catheter in a substantially sealing relationship whereby fluid leakage from the proximal end of the catheter is inhibited; and at least two actuators extending generally outwardly from the proximal portion such that when force is applied to the actuators the slot is shifted from a closed orientation to an open orientation.

2. The device as claimed in claim 1, wherein the two actuators each extend outwardly generally radially and an angle between the actuators subtends an arc of about forty five to about one hundred twenty degrees.

3. The device as claimed in claim 1, wherein the two actuators each extend outwardly generally radially and an angle between the actuators subtends an arc of about ninety degrees.

4. The device as claimed in claim 1, wherein the two actuators each extend outwardly more than ninety degrees from a radial extension of the slot.

5. The device as claimed in claim 1, wherein the distal extension portion has a generally conical or frustoconical shape.

6. The device as claimed in claim 1, wherein the distal extension portion is shaped to interface with the catheter by the first end entering the lumen at the proximal end of the catheter and making circumferential contact by apposition with inner walls of the lumen.

7. The device as claimed in claim 1, wherein the first end comprises a substantially pointed termination.

8. The device as claimed in claim 1, wherein the distal extension portion is shaped to interface with the catheter by the first end abutting the end of the catheter substantially without entering the lumen.

9. The device as claimed in claim 1, wherein the first end comprises a blunt termination.

10. The device as claimed in claim 1, further comprising at least one circumferential ridge on the distal extension portion.

* * * * *